US008841239B2

(12) United States Patent
Busnaina et al.

(10) Patent No.: US 8,841,239 B2
(45) Date of Patent: Sep. 23, 2014

(54) PATTERNED NANOSUBSTRATES MADE BY DIRECTED SELF ASSEMBLY OF AMPHIPHILIC MOLECULES

(75) Inventors: Ahmed A. Busnaina, Ashland, MA (US); Joey L. Mead, Carlisle, MA (US); Carol M. F. Barry, Tyngsborough, MA (US); Ming Wei, Lowell, MA (US)

(73) Assignees: Northeastern University, Boston, MA (US); University of Massachusetts, Boston, MA (US)

( * ) Notice: Subject to any disclaimer, the term of this patent is extended or adjusted under 35 U.S.C. 154(b) by 776 days.

(21) Appl. No.: 12/743,441

(22) PCT Filed: Nov. 21, 2008

(86) PCT No.: PCT/US2008/012977
§ 371 (c)(1),
(2), (4) Date: Jul. 27, 2010

(87) PCT Pub. No.: WO2009/075720
PCT Pub. Date: Jun. 18, 2009

(65) Prior Publication Data
US 2010/0311613 A1 Dec. 9, 2010

Related U.S. Application Data

(60) Provisional application No. 61/003,892, filed on Nov. 21, 2007.

(51) Int. Cl.
*G03F 7/00* (2006.01)
*G03F 7/004* (2006.01)
(Continued)

(52) U.S. Cl.
CPC . *B02Y 30/00* (2013.01); *G03F 7/00* (2013.01); *G01N 2035/00158* (2013.01); *G03F 7/004* (2013.01); *B05D 3/141* (2013.01); *B82Y 40/00* (2013.01); *B05D 1/185* (2013.01); *G01N 2033/0096* (2013.01); *B82Y 10/00* (2013.01); *G03F 7/0002* (2013.01); *Y10S 977/888* (2013.01)

USPC .......... 506/39; 435/4; 435/6.1; 435/29; 430/325; 977/888

(58) Field of Classification Search
CPC ......... G03F 7/0035; G03F 7/165; C23C 8/02; G01N 2610/00
USPC ...................... 134/1.1; 510/176; 977/788–791
See application file for complete search history.

(56) References Cited

U.S. PATENT DOCUMENTS 5,512,131 A 4/1996 Kumar et al.
2003/0142901 A1 7/2003 Lahann et al.
(Continued)

OTHER PUBLICATIONS

Baralia et al. (Nanotechnology, 2006, 17:1160-1165).*
(Continued)

*Primary Examiner* — Christopher M Babic
*Assistant Examiner* — Jeremy C Flinders
(74) *Attorney, Agent, or Firm* — McLane, Graf, Raulerson & Middleton, PA (57) ABSTRACT

Nanoscale patterns prepared by lithography are used to direct the self-assembly of amphiphilic molecules to form patterned nanosubstrates having a desired distribution of chemical functional moieties. These patterns can be fabricated over a large area and require no special limitations on the chemistry the assembled amphiphiles. Hydrophilic/hydrophobic patterns can be created and used to direct the deposition of a single functional component to specific regions of the surface or to selectively assemble polymer blends to desired sites in a one step fashion with high specificity and selectivity. The selective deposition of functional moieties on a patterned surface can be based on electrostatic forces, hydrogen bonding, or hydrophobic interactions. The methods and patterned nanosubstrates of the invention can be used in the assembly of functional polymer systems, polyelectrolytes, biomolecules, conducting polymers, colloids and nanoparticles, and find wide technological applications in biosensors, biochips, photonics and electronics.

25 Claims, 10 Drawing Sheets

(51) Int. Cl.
*C40B 60/12* (2006.01)
*B82Y 40/00* (2011.01)
*B05D 1/18* (2006.01)
*B82Y 10/00* (2011.01)
*C40B 40/02* (2006.01)
*C40B 40/06* (2006.01)
*C40B 40/10* (2006.01)
*G01N 35/00* (2006.01)
*B05D 3/14* (2006.01)
*G01N 33/00* (2006.01)

(56) References Cited

U.S. PATENT DOCUMENTS

2004/0180147 A1 9/2004 Parikh et al.
2007/0238010 A1 10/2007 Zhang et al.

OTHER PUBLICATIONS

Wagner et al. (Langmuir, 1995, 11:3867-3875).*
Pallandre et al. (J. Amer. Chem. Soc., 2004, 127:4320-4325).*
Britland et al. (Biotechnol. Prog., 1992, 8:155-160).*
Tsuboi et al. (Applied Physics Letters, 2006, 88:103102:1-3).*
Wei et al. (J. Phys. Chem. B, 2006, 110:24324-24330).*

* cited by examiner

ODT area     patterned MUDA/ODT area

*FIG. 5a*

ODT area     patterned HUT/ODT area

PATTERNED NANOSUBSTRATES MADE BY DIRECTED SELF ASSEMBLY OF AMPHIPHILIC MOLECULES

STATEMENT REGARDING FEDERALLY SPONSORED RESEARCH OR DEVELOPMENT

The research leading to this invention was carried out with United States Government support provided under a grant from the National Science Foundation Grant No. NSF-0425826. Therefore, the U.S. Government has certain rights in this invention.

CROSS REFERENCE TO RELATED APPLICATIONS

This application claims the priority of U.S. Provisional Application No. 61/003,892 filed Nov. 21, 2007 entitled, DIRECTED ASSEMBLY OF POLYMER BLENDS BY SELF ASSEMBLY OF ALKANETHIOLS ON ELECTRON BEAM LITHOGRAPHY PATTERNED TEMPLATES, the whole of which is hereby incorporated by reference.

BACKGROUND OF THE INVENTION

With the rapid development of nanoscience, it is necessary to develop simple and rapid fabrication techniques to create highly ordered functional nanostructures (1-3). Self-assembled monolayers (SAMs) have sparked interest, since the terminal functional group of the SAM bonded to the substrate can modify the surface properties of the bare substrate, for example, to create patterns of hydrophobic or hydrophilic characteristics (4,5). Such chemical surface structures prepared with functionalized SAMs may play an important role in the site-specific immobilization of molecules (6).

Patterned monolayers have been generated by a variety of ways, including by direct patterning or indirect patterning (7,8). The direct patterning approaches include microcontact printing and dip-pen nanolithography (DPN), in which the adsorbates are selectively placed on the surface and then the remaining surface area is backfilled by a second adsorbate or left bare. Previous work on patterning SAMs has focussed primarily on microcontact printing technology (9). This technology is limited, however, by the challenges of achieving high resolution (e.g., line widths of <50 nm) and replication accuracy, due to degradation of the elastomeric stamp and the unbalanced contact pressure applied to the substrate (8). DPN, as another "direct writing" technology to printing SAMs, was demonstrated by Mirkin's group (10,11). With DPN, the preparation of patterned features has been explored down to 15 nm line width and is controlled by a complex mixture of factors, such as the tip-substrate contact time, relative humidity, and scan speed (12). Unfortunately, the speed of writing with an atomic force microscope (AFM) tip as practiced with DPN is quite slow, and scale-up requires the development of multiple scanning probe tips to enable paralleling processing (13).

In indirect patterning, the molecules from a pre-existing SAM are removed, reacted or destroyed using AFM, scanning tunneling microscopy (STM) or an energetic beam, followed by back filling the bare areas by a second adsorbate (3,8). A typical example is nanografting (14). Liu et al. patterned alkanethiolate SAMs by selective removal of adsorbates either by applying a mechanical force with an AFM tip or by sending high energy electrons from the tip to the substrate using STM (15,16). Again, as with DPN, this method is limited by the slow nature of these processes. In addition, a key issue is control of the normal force, which is often difficult to adjust experimentally and is theoretically calculated. Energetic beams have also been used to destroy or react selected portions of pre-existed SAMs (17-19). For example, Sun, et al. used Ultra-violet (UV) radiation to selectively remove portions of a SAM made of 11-mercaptoundecanoic acid and then backfilling using n-dodecanethiolate to obtain a patterned SAM. Grunze and coworkers (20) irradiated a 4'-nitro-1,1'-biphenyl-4-thiol (NBT) preabsorbed gold substrate with 50 eV electrons through transmission electron microscopy (TEM) grids to reduce nitro groups in the exposed area to amino groups, and then used n-dodecanethiol to replace the NBT in the unexposed area to form patterned SAMs with different functional groups. Craighead, et al. have demonstrated patterning with bi-component SAMs with $NH_2$— and $CH_3$— termini using a low energy electron beam to irradiate a methyl-terminated SAM followed by backfilling the damaged areas with cysteamine generated SAMs (21). These patterning methods involving the oxidation or reduction of SAMs by an energetic beam depend, however, on the sensitivity of a particular SAM to irradiation, which limits the range of accessible chemical functionalities.

Polymeric materials, particularly block copolymers and blends, haven been investigated because of their ability to self assemble into a variety of interesting and useful morphologies (22). These morphologies can be used as flexible templates for assembly of nanodevices (23) that are appropriately modified to "mate" with the block copolymer (24,25). In order to obtain long range order in block copolymers, techniques such as nanopatterned surfaces (26,27) and electric fields (28,29) have been used. Chemically modified surfaces have also been used to prepare defect-free nanopatterns over large areas (30). Although certain approaches have been demonstrated, the methods are often unsuitable for scale-up. For example, long annealing times are typically necessary, making the approach impractical for high rate, high volume processing methods. In order to make this approach viable for commercial products, the ability to obtain the desired structure over large areas in a high rate, high volume process is required. Additionally, many approaches focus on patterning of block copolymers; however, this approach is limited in that the pattern spacing is dictated by the polymer structure.

Another previously described technique involves the patterning of silane monolayers (34). However, that method is limited by the high electron sensitivity and chemical and physical stability required of the PMMA resists in the silanation process, which must be stable to high temperatures and long reaction times.

BRIEF SUMMARY OF THE INVENTION

The invention provides a method of fabricating a patterned nanosubstrate. The method includes the steps of: (a) providing a substrate coated with a resist layer; (b) forming a nanoscale pattern in the resist layer by lithography, wherein the pattern contains one or more first regions essentially devoid of resist and one or more second regions comprising resist; (c) forming a monolayer of first amphiphiles in the one or more first regions by self assembly; and (d) removing resist from the one or more second regions. In certain embodiments, a monolayer of second amphiphiles is subsequently formed in the one or more second regions. One or more functional agents can then be coupled to the distal ends of at least a portion of the first or second amphiphiles. The functional agents can be, for example, antibodies, enzymes, proteins, ligands for cell surface receptors, nucleic acids, cells or other agents, for example when the nanosubstrate is used in a biosensor or biochip. Structural agents such as polymers can also be coupled to the first or second amphiphiles using chemical properties such as hydrophobicity/hydrophilicity, charge, or other chemical interactions.

Another aspect of the invention is a patterned nanosubstrate. The nanosubstrate includes a substrate, a metal layer superimposed on the substrate, and a layer of a first amphiphile superimposed on the metal layer. The first amphiphile layer is disposed within one or more first regions according to a nanoscale pattern established by lithography. In certain embodiments the nanosubstrate also includes a layer of a second amphiphile disposed within one or more second regions interspersed between the first regions. The nanosubstrate can further include one or more functional agents coupled to the distal ends of at least a portion of the first or second amphiphiles. The functional agents can be, for example, antibodies, enzymes, proteins, ligands for cell surface receptors, nucleic acids, cells or other agents. The nanosubstrate can also be coupled to one or more structural agents such as polymers or conductive leads joined to the first or second amphiphiles.

Other features and advantages of the invention will be apparent from the following description of the preferred embodiments thereof and from the claims, taken in conjunction with the accompanying drawings.

BRIEF DESCRIPTION OF THE DRAWINGS

FIGS. 6A-6D show FESEM images of polystyrene/poly(acrylic acid) blends patterned into non-uniform geometries. FIG. 6A shows 90° bends; FIG. 6B shows T-junctions; FIG. 6C shows a square array; and FIG. 6D shows a circular array.

DETAILED DESCRIPTION OF THE INVENTION

Nanosubstrates can be used to control nanoscale morphology in high rate/high volume manufacturing methods. The inventors have developed a method for making patterned nanosubstrates having different chemical functionalities by combining lithographic methods and self-assembly of amphiphilic molecules. The resulting patterned nanosubstrates can then be used to assemble patterned structures, for example, from polymer blends, functionalized nanoelements, or mixtures of biomolecules or cells. The method and patterned nanosubstrate of the invention can be used, for example, in nanodevices and biosensors.

The approach can be divided conceptually into two steps, top-down and bottom-up. In the top-down portion of the process, a nanolithography method such as electron beam lithography (EBL) is performed on a substrate to produce a positive nanoscale resist pattern, e.g., using polymethyl methacrylate (PMMA) as the resist material. In the bottom-up portion of the process, a first amphiphile (e.g., a hydrophilic alkanethiol) is assembled on the patterned regions exposed by lithography. After the resist is removed, a second amphiphile (e.g., a hydrophobic alkanethiol) is backfilled in the bare areas vacated by the resist. Finally, a mixture of functional or structural elements (e.g., a PS/PAA blend) can be assembled on the patterned amphiphiles, for example by spin-coating the patterned nanosubstrate with a solution containing the functional or structural elements.

A method of fabricating a patterned nanosubstrate according to the invention includes providing a substrate that is coated with a resist layer; forming a nanoscale pattern in the resist layer by lithography, wherein the pattern comprises one or more first regions essentially devoid of resist and one or more second regions comprising resist; forming a monolayer of a first amphiphile in the one or more first regions by self assembly; and removing the resist from the one or more second regions. The process of resist removal can be accomplished by dissolving the resist with a solvent, under conditions that leave the monolayer of first amphiphile essentially intact. Optionally, a monolayer is then formed by self assembly of a second amphiphile in the one or more second regions after the resist has been removed. Another optional step is the addition of one or more functional or structural agents to the surface of the monolayer formed by the first and/or second amphiphiles. This can be facilitated through the placement of specific chemical substituents at the distal (e.g., hydrophilic) ends of the first and/or second amphiphiles. The substrate may or may not contain one or more base layers or other layers. The first and second regions together can occupy the entire surface of the nanosubstrate, or less than the entire surface.

A patterned nanosubstrate according to the invention includes a substrate, a metal or other coating layer superimposed on the substrate, and a nanopatterned layer of a first amphiphile superimposed the metal layer. The first amphiphile layer is disposed within one or more first regions according to the nanoscale pattern, which is established by lithography. In some embodiments, the nanosubstrate further includes a layer of a second amphiphile disposed within one or more second regions. The second regions are interspersed between the first regions. In some embodiments, one or more functional agents are attached at the distal ends of at least a portion of the first and/or second amphiphiles. The substrate may or may not contain one or more base layers or other layers. The first and second regions together can occupy the entire surface of the nanosubstrate, or less than the entire surface.

A precursor patterned nanosubstrate according to the invention includes a substrate, a metal or other coating layer superimposed on the substrate, a nanopatterned layer of a first amphiphile superimposed on the metal layer and disposed within one or more first regions on the substrate, and a resist disposed within one or more second regions on the substrate. The second regions are interspersed within the spaces between the first regions. The substrate may or may not contain one or more base layers or other layers. The first and second regions together can occupy the entire surface of the nanosubstrate, or less than the entire surface. The precursor can be converted into a finished patterned nanosubstrate by removing the resist, e.g., by dissolving the resist with a solvent.

The invention also includes kits containing one or more components of the invention together with packaging material and instructions for using the components. In one embodiment, a kit contains a precursor patterned nanosubstrate and instructions for removing the resist material and adding a second amphiphile monolayer provided by the user. In another embodiment, a kit contains a patterned nanosubstrate that is devoid of functional agents, but is surface-derivatized with appropriate chemical groups (e.g., amino groups or other functional groups), together with instructions so that the user can couple one or more desired functional agents to the surface of the patterned nanosubstrate.

In contrast to previous approaches, by making use of conventional lithographic techniques such as EBL, the approach of the present invention is not limited to specific functional groups, such as photosensitive groups, or to the reaction conditions required for other patterning methods such as electron irradiation. The present invention allows a large variety of SAMs to be patterned, because the lithography approach establishes mechanical limits to self association of amphiphilic molecules in creating a patterned SAM on the substrate. In addition, the approach described here has the benefit of using general resists such as PMMA, which function over a wide range of temperature and humidity, for example. Further measures, such as the use of ethanol in the monolayer assembly process, prevent swelling or dissolution of the PMMA resists, resulting in patterned features with very high resolution and quality. This technology provides a route capable of creating nanopatterned SAMs with ultrahigh resolution down to the range of less than 10 nm.

In one embodiment, a nanoscale pattern is formed containing hydrophilic amphphiles in a first region of the substrate and hydrophobic amphiphiles in a second region of the substrate. While all amphiphilic molecules include at least one hydrophilic portion and at least one hydrophobic portion, as used herein the term "hydrophilic amphiphile" refers to an amphiphile that, when assembled to form a monolayer on a substrate surface exposes a hydrophilic portion or functional group into the medium above the substrate, and a "hydrophobic amphiphile" refers to an amphiphile that, when assembled to form a monolayer on substrate surface exposes a hydrophobic portion or group into the medium above the substrate. Functional groups exposed by the amphiphiles of a SAM to the medium can be employed to selectively assemble, for example, single component macromolecules to desired areas of the substrate.

One significant advantage of the present method is the ability to control the site-specific deposition of polymer blends or other mixtures of functional moieties using a chemically patterned surface through secondary interactions. Another advantage is that the selective assembly process can be accomplished in a short period of time, as little as 30 seconds, and does not require the long annealing time required, for example, in the conventional assembly of block copolymers and polymer blends. Furthermore, the resulting polymeric structures can be patterned over a very large area and high resolution, consistent with the limits of photolithography or EBL. This affords a significant advantage over the limited area of assembly provided by DPN and over the low resolution provided by microcontact printing. Therefore, the present method provides a path towards the processing of polymeric nanostructures at high rates and high volumes. The polymeric structures produced according to the invention can have multiple surface functionalities and can be used in fabrication of, for example, microphotonic arrays and biosensors.

In the method of the present invention, the pattern is drawn by a lithography method, such as EBL patterning of a PMMA resist. This technology is versatile, because it is capable of patterning a wide variety of amphiphiles, such as conventional alkanethiols, and it is not limited to amphiphiles with specific functional groups, for example as required for patterning by electron radiation. In addition, this process does not have restrictive chemical or physical property requirements for the resist material as in the patterning of silane SAMs. Since the patterning of SAMs is based on the patterning of a resist by lighography, this approach has the potential to reach ultrahigh resolution down to the limits of lithography techniques, or down to 10 nm or less. The invention also provides the ability to pattern SAMs over large areas and with high throughput, comparable to the production of microelectronics. The binary hydrophilic/hydrophobic patterns that can be generated by this method can be used to assemble macromolecules or polymer blends to form functionally complex surfaces.

Patterned nanosubstrates of the invention can be used to direct the assembly of polymers to form macromolecules, arrays or complexes of macromolecules, or other higher order structures. This directed assembly can be based on electrostatic forces, hydrogen bonding, hydrophobic forces, as well as van der Waals forces. A desired distribution of amphiphiles with certain chemical properties can be established on a substrate using the methods outlined above. Such amphiphiles include hydrophilic/hydrophobic amphiphiles, amphiphiles carrying positive or negative charge at or near their distal ends, and amphiphiles bearing groups such as hydroxyl or carboxyl groups that participate in hydrogen bonding.

The top layer of a patterned nanosubstrate, i.e., the surface that can interact with a solution or test sample placed upon it, can be derivatized to add one or more functional agents. Such functional agents include peptides, proteins, antibodies and their antigen binding fragments, recombinant or engineered proteins, enzymes, ligands for cell surface receptors, nucleic acids, oligonucleotides, and even whole cells. Functional agents provide the patterned nanosubstrate the ability to sense specific molecules in their vicinity and can enable a patterned nanosubstrate to function as a biosensor. Functional agents can also be used to carry out chemical reactions on the surface of the nanosubstrate, enabling it to serve as a nanoreactor or to carry out analytical techniques. By creating an appropriately designed nanoscale pattern by lithography, functional groups can be arranged in any desired pattern in order to carry out sequences of reactions or to allow the functional interaction of functional agents.

It should be noted that the directed assembly process described above is another level of self assembly, and in at least some cases it can occur very rapidly, e.g., during the course of a 30 second spin coating process, and generally doesn't require any time consuming annealing process. The high specificity and selectivity between macromolecules and chemical functional groups make this process useful for fabricating binary component polymer arrays on a single patterned surface at a high rate, which is critically important to reduce the cost of nanomanufacturing. Using high resolution techniques such as ESL, the smallest features of nanopatterns that can be established on a substrate with the present methodology is expected to be as small as 10 nm or less. In this regard it should be noted that if the nanopattern is to direct the assembly of a mixed phase system (e.g., a hydrophilic/hydrophobic polymer blend like PS/PAA), the phase domain size of the system applied to the nanopattern can be limiting. Only when the phase domain size is well matched with the pattern size can highly selective assembly be obtained. Some systems have a phase domain size (e.g., PS/PAA has a phase domain size of 300-500 nm) that is much larger than the feature size of the nanopattern. By changing the polymer system or adding a compatibilizer, the phase domain size can be changed (reduced), thereby improving the resolution of directed assembly.

Substrate Material

The substrate can be formed of a single homogeneous material or it can be formed from a layered assembly or other assembly of different materials. Any material suitable for use in nanodevices, electronics, photonics, or biosensor applications can be used. For example, the substrate can contain a base layer of silicon, silicon dioxide, a polymer, or other materials. For implementations involving electrically conductive layers or components, the base layer or the entire substrate is preferably formed from any non-conductive material. The base layer can be optionally coated with one or more conducting or non-conducting layers. Conducting layers can be formed by depositing a metal such as gold, silver, copper, or chromium using known methods, such as evaporation or sputtering. The thickness of the base layer and any additional layers or regions can be tailored to suit the desired application. Conducting layers will typically be in the nm range, e.g., from about 1 nm to about 1000 nm, or from about 1 nm to about 500 nm, or about 50 nm to about 150 nm, and preferably in the range from about 10 nm to about 100 nm, such as about 75 nm.

Lithography

Prior to fabrication of self assembled monolayers of one or more amphiphiles on the nanosubstrate, a nanoscale pattern is established in a layer of a resist material using a lithography method. Any available method can be used that is capable of establishing a pattern having nanoscale features in the range from about 1 nm to about 1000 nm, or about 1 nm to about 500 nm, or about 50 nm to about 200 nm, preferably in the range of about 10 nm to about 100 nm, or about 100 nm to about 150 nm. For example, the method can be electron beam lithography, ion beam lithography, photolithography (also known as optical lithography, or nanoimprint lithography.

Electron beam lithography (EBL) is a well-established patterning technology capable of creating extremely fine patterns down to at least 10 nm due to the very small spot size (~2 nm) of the electrons (31). Compared to other lithographic processes, it combines high resolution with high reliability and reasonable patterning speed, therefore, it is widely used in the modern electronics industry for integrated circuits. In a general EBL process, an electron beam scans across the substrate surface covered with an electron sensitive resist layer, such as a PMMA resist, to write a previously programmed pattern; afterwards, the exposed PMMA regions are removed from the substrate by the developer, and then the desired magnetic or metal material is deposited on top of this PMMA template. Finally, a lift-off process is carried out and the materials are patterned on those regions which have been previously defined by the electron beam.

The type of resist material used will depend on the lithography method. The resist can be, for example poly (methyl methacrylate) (PMMA) for EBL, or a photoresist for photolithography. An imprint resist can be used to carry out nanoimprint lithography. Regardless of which lithography technique is used, the resist preferably is hydrophobic and capable of being removed after assembly of the first amphiphile using a solvent, such as an organic solvent (e.g., acetone, hexane, an alcohol, a chlorohydrocarbon, or a mixture thereof). The thickness of the resist material can be determined by the particular application, but is preferably selected to approximately match, or be somewhat greater than, the thickness of the monolayer of first amphiphile. For example, the thickness of the resist layer can range from about 10 nm to about 50 nm, or from about 50 nm to about 200 nm, or more, or can be about 100 to about 150 nm.

Amphiphiles

Amphiphilic molecules that are capable of self assembly will have at least one portion that is hydrophilic and at least one portion that is hydrophobic. Self assembly generally involves the association of hydrophobic groups together to form a hydrophobic region, and may also involve electrostatic, hydrogen bonding, or other non-covalent or covalent interactions between the hydrophilic portions of the amphiphiles. Amphiphiles may have certain chemically reactive groups in any portion of the molecule. Preferably, an amphiphile has a reactive group at one end that can react with the substrate. For example, amphiphiles can possess a terminal or near terminal thiol group capable of reacting with a gold surface on the substrate. Amphiphiles may or may not have one or more additional reactive groups. For example, they may have amino groups or other groups including carboxyl groups, sulfhydryl groups, or hydroxyl groups at or near the terminal portion that extends away from the substrate and into the medium (e.g., air or an aqueous solution) that is disposed above the surface of the substrate.

In some embodiments, the substrate is hydrophobic, or is coated with a hydrophobic material, and the amphiphiles will generally adhere to the substrate or its coating by hydrophobic interactions, but also can be covalently linked to the substrate or its coating through a reactive group (e.g., a thiol group reacting with a gold coated substrate). Covalent linkage to the substrate or its coating is preferred, and the particular chemical group added to the terminus of the amphiphile will depend on the surface chemistry of the substrate. In these embodiments, the other end of the amphiphile contains a polar head group, such as a charged or other hydrophilic substituent (e.g., an amino group, carboxyl group, hydroxyl group, or one or more sugar molecules). The hydrophilic substituent will permit the patterned nanosubstrate to be wetted and to interact with aqueous solutions and their molecular components. Mixtures of hydrophilic and hydrophobic amphiphiles can be arranged into a two-dimensional pattern to establish one or more regions on the nanosubstrate where aqueous solutions will or will not interact with the substrate, as desired for the particular application. For example, square, rectangular, or circular patterns of hydrophilic amphiphiles surrounded by hydrophobic amphiphiles can be used to establish a nanoarray containing nanowells for use in sensors or analytical chips.

A group of suitable amphiphiles for use with the invention is shown in Table 1.

TABLE 1

Structures of some exemplary alkanethiols

| 11-Amino-1-undecanethiol, hydrochloride |  |
|---|---|

TABLE 1-continued

Structures of some exemplary alkanethiols

11-Mercaptoundecanoic acid

11-Hydroxy-1-undecanethiol

The following examples are presented to illustrate the advantages of the present invention and to assist one of ordinary skill in making and using the same. These examples are not intended in any way otherwise to limit the scope of the disclosure.

Materials

11-Amino-1-undecanethiol hydrochloride with 99% purity and 11-Hydroxy-1-undecanethiol with 97% purity were purchased from Asemblon, Inc. 11-Mercaptoundecanoic acid with 97% purity and 1-octadecanethiol with 98% purity were purchased from Aldrich. Polystyrene standard with 20,000 $M_w$, poly (acrylic acid) with 2,000 $M_w$, and the solvents including hexane, acetone, anhydrous ethanol and N,N-dimethylformamide were purchased from Aldrich.

Methods

Substrate Preparation:

PMMA trench patterns (300 nm wide with 700 nm spacing) were created on a gold substrate as follows. A 120 nm thick Au layer was evaporated onto a Si (100) wafer with 5 nm thick Cr as an adhesion layer. The PMMA resist with 150 nm thickness was spin-coated onto the Au substrate. Electron beam lithography (EBL) was used to write previously programmed patterns on the PMMA film. The exposed PMMA regions were developed using MIBK solution and then treated with oxygen plasma for 5 seconds to remove the residual PMMA resist at the bottom of the PMMA trench.

Patterning of Alkanethiols:

After the template with PMMA pattern was cleaned by plasma, it was immersed into 1 mM 11-amino-1-undecanethiol hydrochloride or 11-hydroxy-1-undecanethiol, or 11-mercaptoundecanoic acid for 24 hours to form well-ordered hydrophilic SAMs at the PMMA trench area. Afterwards, the template with assembled SAMs was washed with ethanol several times to remove any additional layers of alkanethiol situated on the top of the monolayer deposited on the substrate surface. Afterwards, the template was extracted with acetone using a Soxhlet extractor for 24 hours to completely remove any remaining PMMA resist in the second area. Finally, the template was immersed in 1-octadecanethiol for 24 hours to grow well-ordered hydrophobic alkanethiols on the remaining gold area, i.e., the spacing area of the original PMMA pattern.

Patterning of Polystyrene (PS), Poly(Acrylic Acid) (PAA) or Polystyrene/Poly(Acrylic Acid) Blends:

Once the secondary thiol treatment was finished, the chemically patterned template was immediately put on the rotating plate of a spin coating machine prefilled with high purity nitrogen gas, and a droplet of polymer solution, such as 1 wt % PS in DMF, 1 wt % PAA in DMF or 1 wt % PS/PAA with a 70/30 ratio in DMF, was placed on the top of the pattern area of the template. After remaining quiescent for 5 minutes, the polymer solution was spin-coated on the template surface at 3000 rpm rotation speed for 30 seconds. With the evaporation of DMF, PS, PAA or PS/PAA blends were assembled on the chemically patterned template.

Extraction of PS Phase:

The patterned PS/PAA film was immersed in hexane, a solvent of PS and a non-solvent for PAA, for 24 hours to remove the PS phase.

Characterization

Field emission scanning electron microscopy (FESEM) images and EDS were performed using a JEOL 7401F field emission scanning electron microscope. FMM images of patterned PMMA resists were examined using scanned probe microscopy (Veeco NanoScopella, PSIA XE-150 mode, 40N/m tip spring constant). Phase images of patterned alkanethiols were examined using tapping mode AFM. Topographic images of patterned PS/PAA films before and after hexane treatment were done using non-contact mode AFM.

Example 1

Patterning of Hydrophilic/Hydrophobic Alkanethiols

Figure 1:
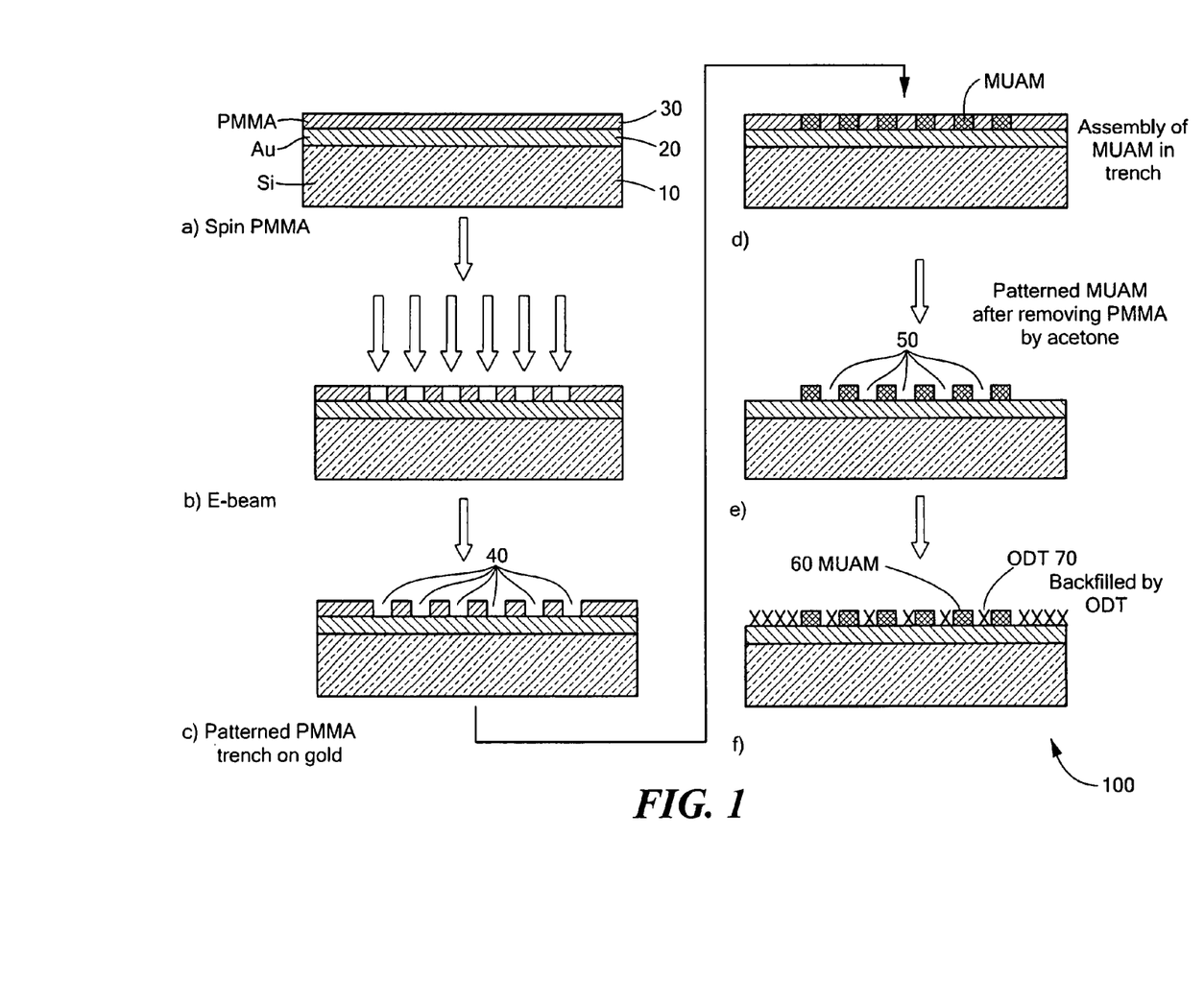
FIG. 1 shows a schematic diagram of patterning of hydrophilic/hydrophobic alkanethiols combining EBL and self-assembly of alkanethiol molecules. a) ~150 nm thick PMMA resist spin coated onto the gold deposited on a silicon wafer; b) & c) patterned PMMA trenches defined by electron beam and development; d) a hydrophilic 11-Amino-1-undecanethiol, hydrochloride (MUAM) assembled in the PMMA trench area; e) patterned MUAM after PMMA resists removed by acetone; f) backfilled by hydrophobic 1-octadecanethiol (ODT) yielding the final chemical pattern.

PMMA resists on a gold substrate were patterned using EBL, and self-assembly of thiol molecules was used to create patterned alkanethiol monolayers. FIG. 1 shows a schematic diagram of the process used to pattern hydrophilic and hydrophobic alkanethiols. To begin the process, initial PMMA resist layer 30, about 150 nm thick, was spin-coated onto gold layer 20 deposited on substrate base layer 10. Next, the positive PMMA resist line patterns were formed by EBL, followed by 5 seconds of oxygen plasma treatment. The hydrophilic MUAM monolayers then were assembled on the exposed gold surface at the bottom of PMMA trenches 40 by immersing the template in a thiol solution for 24 hours. After thiolation, the remaining PMMA resist was removed by Soxhlet extraction using acetone for 24 hours to expose the gold surface. Finally, the hydrophobic ODT monolayers were assembled onto exposed gold area 50, yielding a pattern with different chemical functionality. The finished patterned nanosubstrate 100 was covered with first regions 60 of MUAM adjacent to second regions 70 of ODT.

Figure 2A:
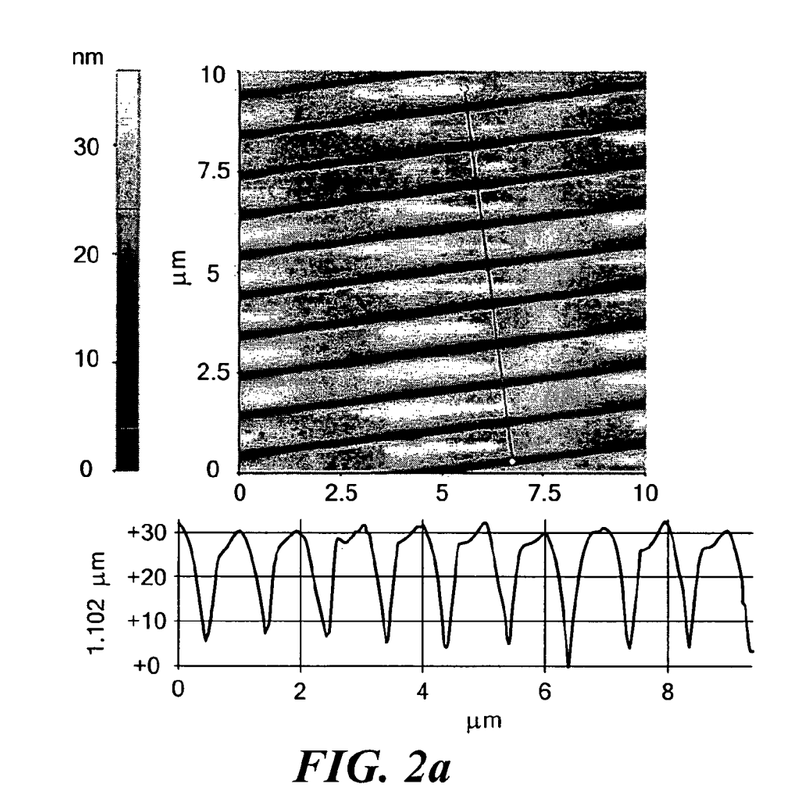
FIGS. 2A-2B show force modulation microscopy (FMM) and field emission scanning electron microscopy (FESEM) images of the patterned PMMA resist after development and plasma treatment.
Figure 2B:
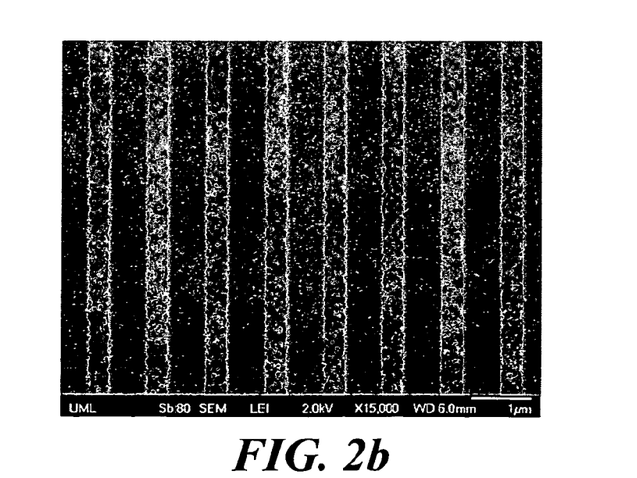
Figure 2C:
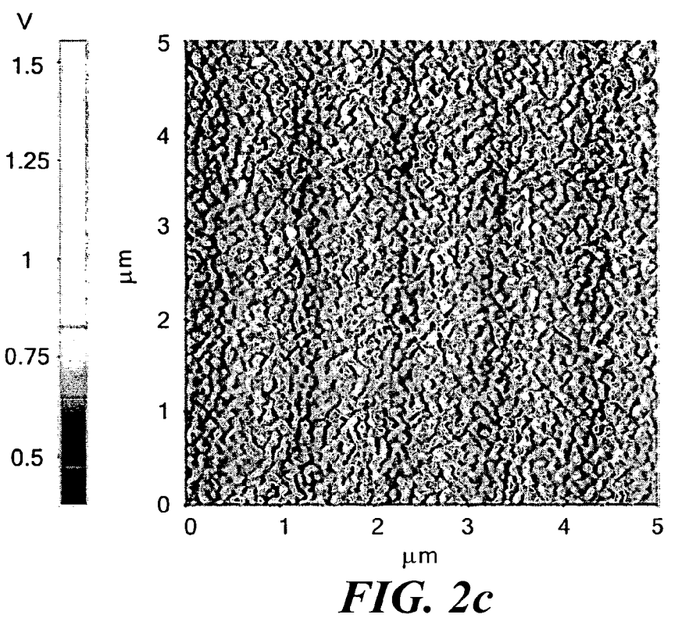
FIG. 2C shows lateral force microscopy (LFM, contact mode) of MUAM ($-NH_3^+$) lines after PMMA removal.
Figure 2D:
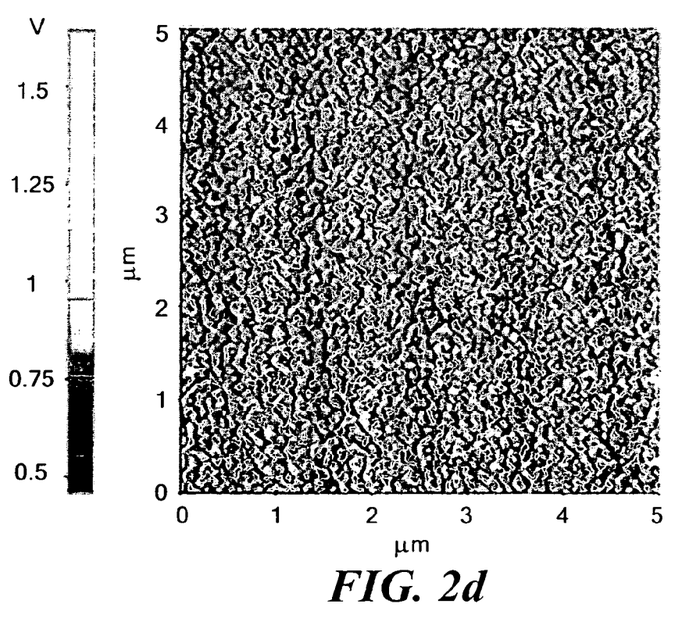
FIG. 2D-2E show LFM (contact mode) and FESEM images of binary patterned monolayers consisting of hydrophilic MUAM ($-NH_3^+$) (shown as dark) and hydrophobic ODT ($-CH_3$) (shown as light).
Figure 2E:
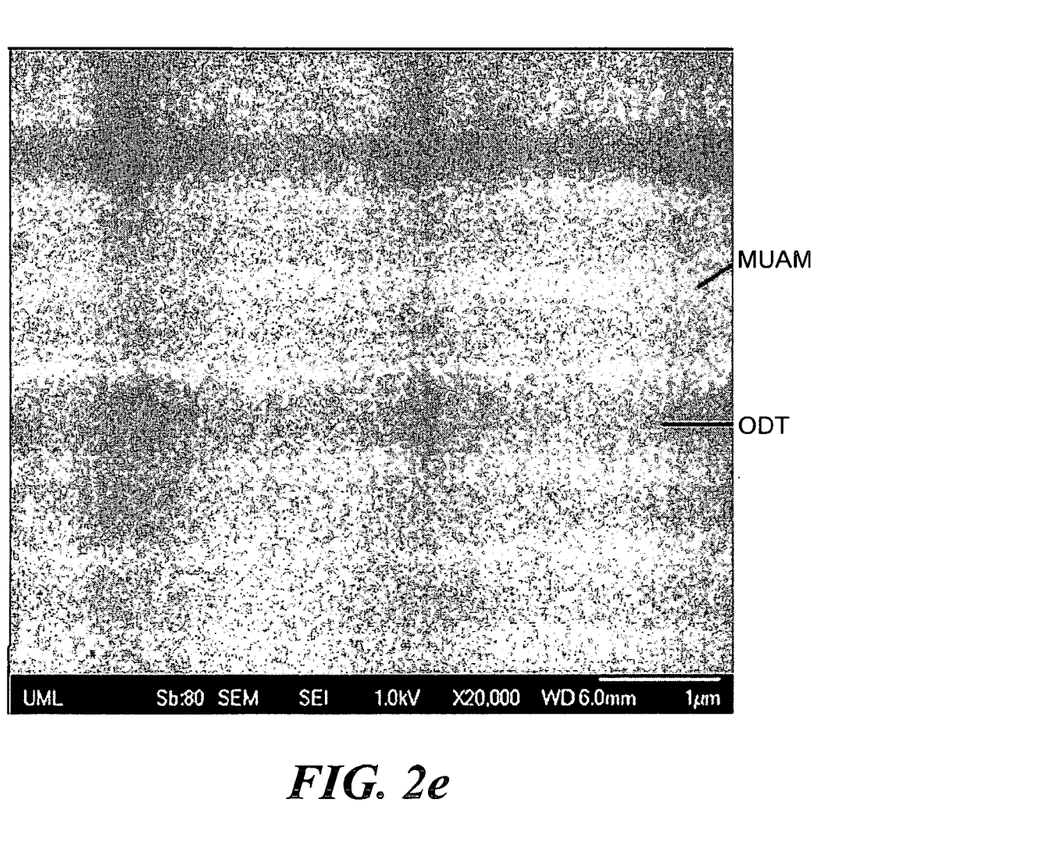

It should be noted that a clean gold surface on both the trench bottom and the area after PMMA removal is critical for the formation of well ordered SAMs. Efforts to pattern the SAMs without plasma treatment were unsuccessful. Therefore, before the thiolation of the first SAM, the PMMA trench template was treated by oxygen plasma for 30 seconds in order to get rid of the residual PMMA debris formed during the development process. FIGS. 2a and 2b show the FMM and FESEM images of the PMMA resist pattern on the gold surface after plasma treatment. The thickness of the PMMA resist was around 30 nm. Similarly, before the thiolation of the secondary SAM, the PMMA resist on the space area has to be completely removed to guarantee a clean gold surface. Soxhlet extraction with acetone was carried out for 24 hours to remove all of the PMMA resist. Energy Dispersive Spectroscopy (EDS) of the template after extraction demonstrated the complete removal of PMMA resist. FIG. 2c shows the LFM image of patterned MUAM stripes on the gold surface after PMMA removal; the image shows the same pattern as the original PMMA resist pattern. FIG. 2d shows the LFM image of patterned MUAM/ODT monolayers after patterned MUAM was backfilled with ODT monolayers. The force difference between the tip and MUAM or ODT produced different contrast, replicating the same pattern as PMMA resist. The patterned MUAM/ODT monolayers were also verified in the FESEM image as shown in FIG. 2e. MUAM has higher electron density than ODT due to the terminal amino functional group. As a result, the increasing scattering of secondary electrons of MUAM is expected to generate the lower brightness compared to ODT in the image. The better ordering of alkane chains in ODT than MUAM monolayers also contributed to the higher brightness of ODT SAMs in the image. The increased order for longer chains in the ODT monolayer caused reduced interfacial free energy. Hence, the lower content of absorbed contaminants on the ODT region make the surface appear brighter (32,33).

Example 2

Direct Assembly of Macromolecules by Patterned MUAM/ODT Monolayers

Figure 3A:
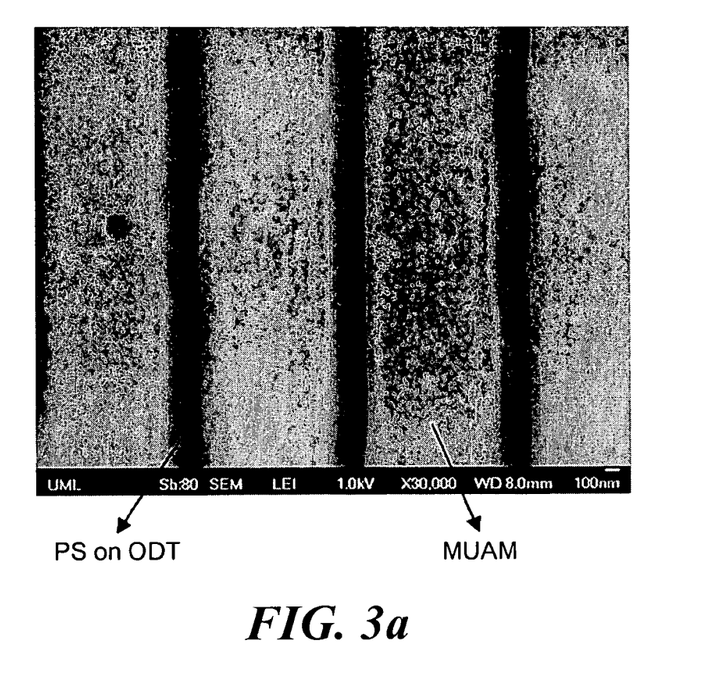
FIGS. 3A and 3B show FESEM images of patterned polystyrene (FIG. 3A) and poly(acrylic acid) (FIG. 3B) assembled by patterned MUAM ($-NH_3^+$)/ODT ($-CH_3$) monolayers.
Figure 3B:
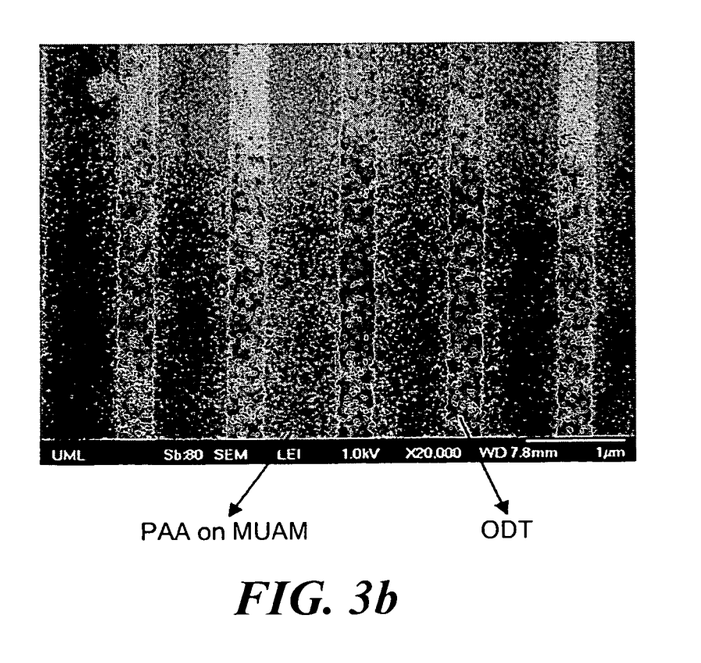

In order to evaluate the use of a hydrophilic/hydrophobic monolayer pattern to serve as a template for polymer assembly into larger structures, a single polymer component (either a polystyrene (PS) or poly(acrylic acid) (PAA) solution) was spin-coated onto a gold template similar to that described in Example 1, patterned with alternating hydrophilic MUAM and hydrophobic ODT monolayers. As shown in FIG. 3a, the PS was deposited onto the ODT strips with high selectivity. It is assumed that the hydrophobicity was the main driving force in directing PS to the hydrophobic ODT regions in this experiment. However, selective assembly on a monlayer coated, patterned nanosubstrate also could be driven by electrostatic forces. PAA is a weak polyanion that would be absorbed on surfaces with cationic characteristics. Thus, a positively charged alkanethiol can be used to guide PAA to a desired site on the substrate surface. FIG. 3b shows that PAA was selectively absorbed to the MUAM regions containing a positively charged $NH_3^+$ terminal group. Some small defects, which are believed due to contamination, are visible in the images. Such defects can be prevented by the use of a clean room for monolayer assembly and polymer assembly. The highly selective assembly of each single component of PS and PAA not only demonstrated the functionality of this hydrophilic/hydrophobic pattern, but also indirectly demonstrated the regularity of the patterned thiols.

Example 3

Figure 4A:
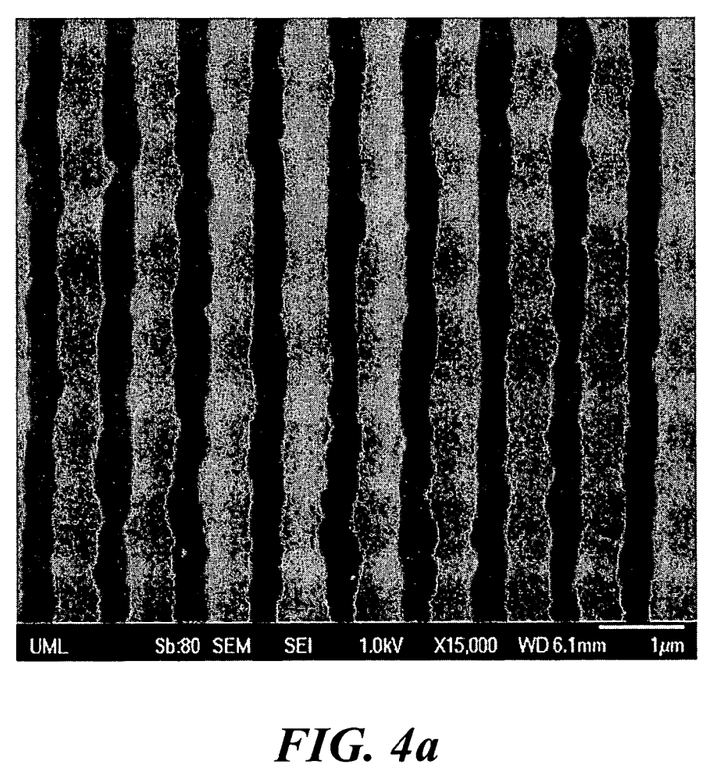
FIG. 4A shows an FESEM image of patterned polystyrene/poly(acrylic acid) assembled by patterned MUAM ($-NH_3^+$)/ODT ($-CH_3$) monolayers.
Figure 4B:
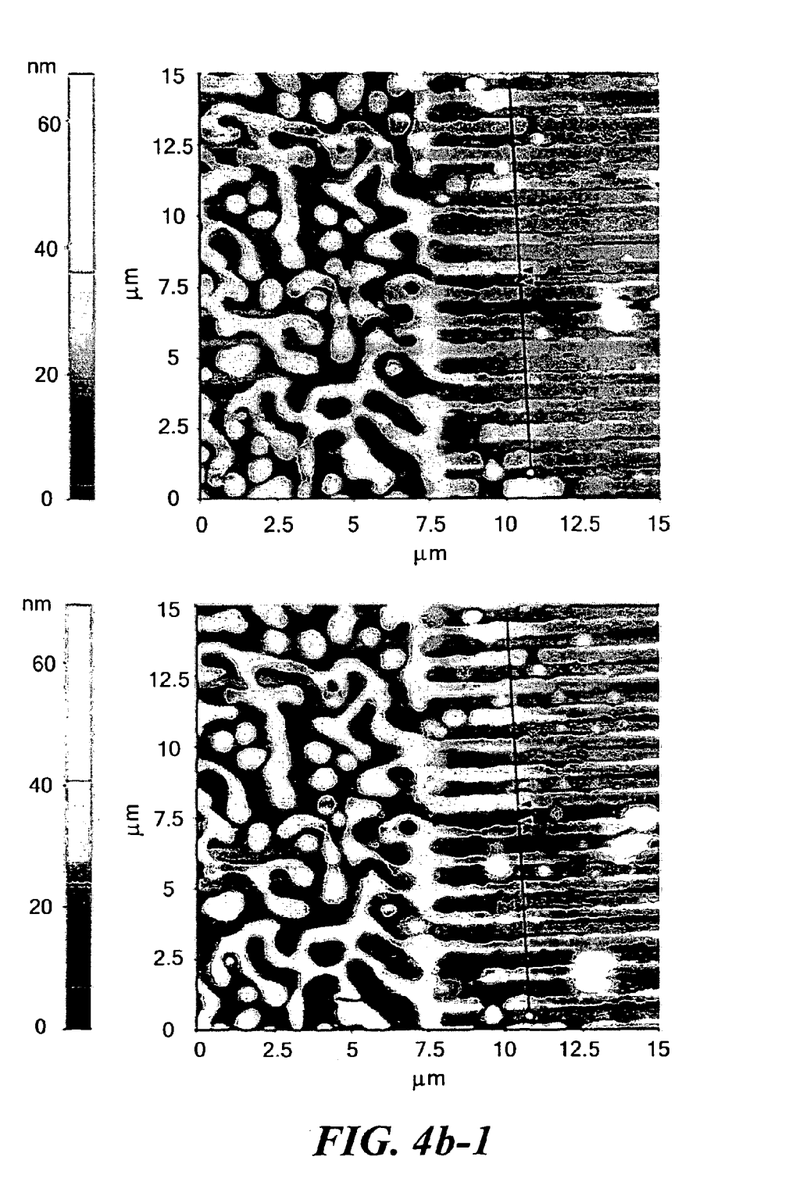
FIG. 4B shows AFM topographic images of patterned polystyrene/poly(acrylic acid) before and after washing by hexane and the corresponding height information for the blue line shown on the right side.
Figure 4B:
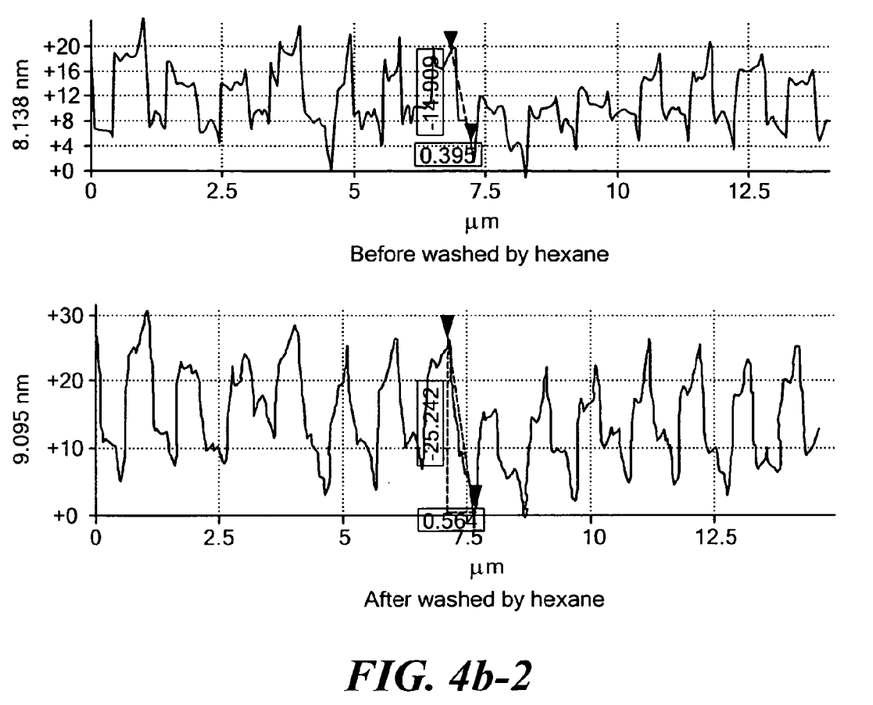

Direct Assembly of PS/PAA Blends by Patterned Hydrophilic/Hydrophobic Monolayers A further demonstration of the use of a hydrophilic/hydrophobic pattern such as demonstrated in Example 2 was accomplished by the assembly of PS/PAA blends. A PS/PAA blend with 70/30 composition ratio was spin-coated on a gold template containing patterned MUAM/ODT monolayers with 300 nm/700 nm scale. FIG. 4a shows the presence of a side-by-side PS/PAA film with the dark areas indicating PAA and the light areas indicating PS. In order to prove that the phase separation of PS/PA blends was directed by the chemically patterned surface, the patterned PS/PAA film was immersed in hexane, a solvent of PS and a non-solvent for PAA, for 24 hours to remove the PS phase. FIG. 4b shows the AFM topographic images of the PS/PAA film before and after dissolving the PS phase by hexane. It can be seen that after hexane treatment, the regions occupied by the original PS phase in the image look much brighter due to the removal of the PS phase. In addition, but comparing the corresponding height difference of the film before and after hexane treatment, it was observed that the average height difference was increased by 10.8 nm after the PS phase was dissolved by hexane. The increased height difference and the regular PS/PAA pattern scale replicating the original alkanethiol patterns indirectly demonstrated the highly selective phase separation and assembly of separate PS and PAA patterns from a PS/PAA blend.

Example 4

Effect of Terminal Functional Groups on Assembly of PS/PAA Blends

Figure 5A:
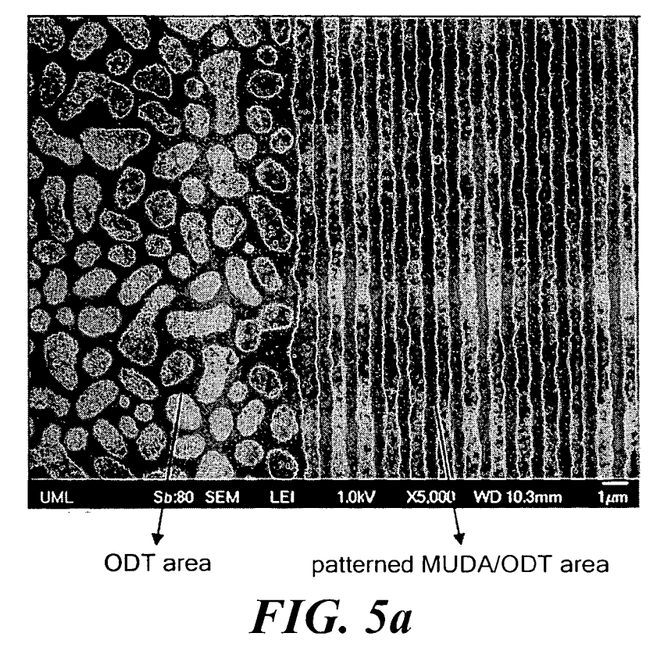
FIGS. 5A and 5B show FESEM images of patterned polystyrene/poly(acrylic acid) blends by patterned MUDA ($-COOH$)/ODT (FIG. 5A) and HUT ($-OH$)/ODT (FIG. 5B).
Figure 5B:
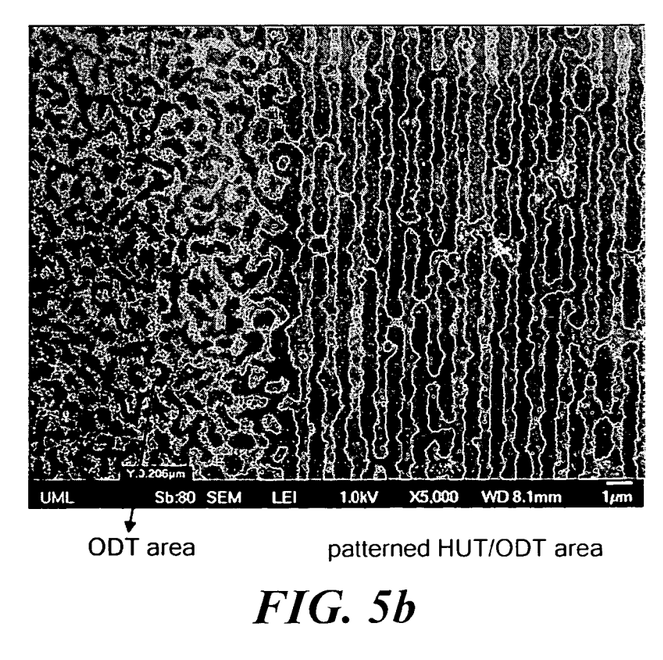

The interactions between SAMs and assembled macromolecules are determined by the terminal functional group of SAMs exposed at the interface. To demonstrate the capability of patterning other types of alkanethiol by this technique and to study the influence of surface functionality on assembly of polymer blends, monolayer surfaces were prepared from 11-mercaptoundecanoic acid (MUDA) (having —COOH terminal groups) and 11-hydroxy-1-undecanethiol (HUT) (having —OH terminal groups) as hydrophilic amphiphiles, in addition to MUAM (having $NH_3^+$ terminal groups). To eliminate any distance effects, all of the hydrophilic thiols had the same alkyl chain length to make the SAMs of similar thickness. Table 1 shows the structures of these three alkanethiols. FIG. 5 shows the FESEM images of patterned PS/PAA films directed by MUDA/ODT and HUT/ODT, respectively. It can be seen that the film patterned by MUDA/ODT has much better order than that by HUT/ODT. The latter shows more defects, including some discontinuous lines and incomplete patterning. The driving force directing the PAA phase onto MUDA or HUT is believed to be the result of hydrogen bonding interactions between the —COOH group of PAA and the —COOH group of MUDA or the —OH group of HUT. The former has stronger hydrogen bonding forces due to the existence of the carboxyl group, resulting in greater forces of attraction for assembling PAA on MUDA as compared to HUT. This resulted in better patterning of the spin-coated PS/PAA blends.

Example 5

Assembly of PS/PAA Blends in Non-Regular Geometries

Figure 6A:
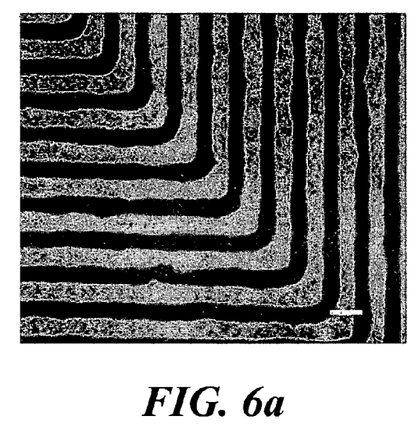
Figure 6B:
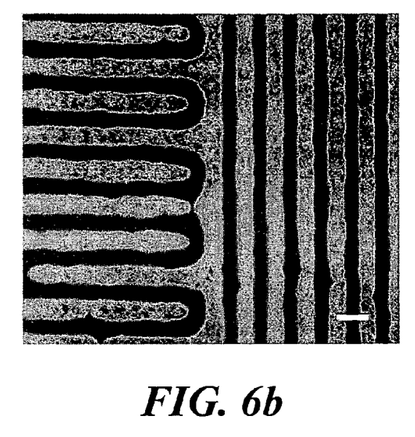
Figure 6C:
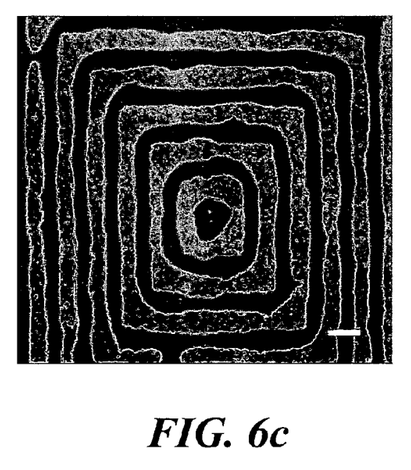
Figure 6D:
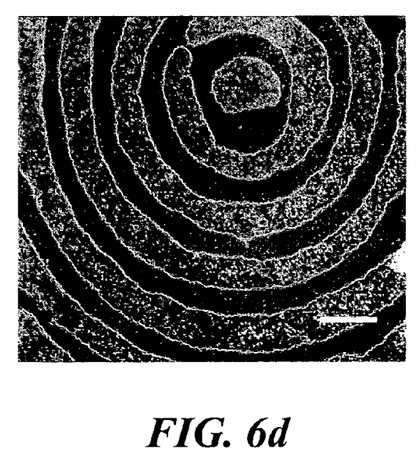

The direct assembly of PS/PAA blends can be used to achieve highly ordered periodic lines over large area in a very short time. However, for many practical applications, including nanolithography, the formation of features with complex and non-regular geometries is important. Examples of desirable non-regular features include square arrays, circular arrays, T-junctions, and 90° bends. FIG. 6 shows a set of complex structures generated by direct assembly of PS/PAA blends. In FIG. 6a, periodic lines with 90° bends were produced having a high degree of order. T-junctions are shown as the light grey areas in FIG. 6b. More complicated square and circular arrays are shown in FIGS. 6c and 6d, respectively. Therefore, by designing the PMMA trench template with the appropriate patterns, direct assembly of PS/PAA blends could easily and rapidly direct the assembly of a variety of complex non-uniform patterns.

The ability to obtain this rapid patterning is due to the strong attraction between the chemically patterned surface (i.e., the substrate-bound amphiphiles) and the added macromolecules (i.e., the functional or structural agents that form a complex with the amphiphiles). In this system, strong interactions result from the hydrophobic interaction between PS and ODT and the electrostatic force between PAA and MUAM. Alternatively, the interactions between SAMs and assembled macromolecules could also be generated by hydrogen bonding or van der Waals forces, which are determined by the terminal functional group or groups of the amphiphiles exposed at the interface.

REFERENCES

1. Aswal, D. K.; Lenfant, S.; Guerin, D.; Yakhmi, J. V.; Vuillaume, D. Analytica chimica Acta 2006, 568, 84.
2. Daniel, M. C.; Astruc, D. Chem. Rev. 2004, 104, 293.
3. Hammond, P. T. Adv. Mater. 2004, 16, 1271.
4. Ulman, A. Chem. Rev. 1996, 96, 1533.
5. Shin, S. K.; Yoon, H. J.; Jung, Y. J.; Park, J. W. Current Opinion in Chemical Biology 2006, 10, 423.
6. Senaratne, W.; Andruzzi, L.; Ober, C. K. Biomacromolecules 2005, 6, 2427.
7. Love, J. C.; Estroff, L. A.; Kriebel, J. K.; Nuzzo, R. G.; Whitesides, G. M. Chemical Reviews 2005, 105, 1103.
8. Smith, R. K.; Lewis, P. A.; Weiss, Paul. S. Progress in Surface Science 2004, 75, 1.
9. Xia, Y.; Whitesides, G. M. Annual Review of Materials Science 1998, 28, 153.
10. Piner, R. D.; Zhu, J.; Xu, F.; Hong, S. H.; Mirkin, C. A. Science 1999, 283, 661.
11. Salaita, K.; Wang, Y.; Mirkin, C. A. Nature Nanotechnology 2007, 2, 145.
12. Haaheim, J.; Eby, R.; Nelson, M.; Fragala, J.; Rosner, B.; Zhang, H.; Athas, G. Ultramicroscopy 2005, 103, 117.
13. Salaita, K.; Lee, S. W.; Wang, X.; Huang, L.; Dellinger, T. M.; Liu, C.; Mirkin, C. A. Small 2005, 1, 940.
14. Liang, J.; Scoles, G. Langmuir 2007, 23, 6142.
15. Xu, S.; Miller, S.; Laibinis, P. E.; Liu, G. Y. Langmuir 1999, 15, 7244.
16. Liu, G.; Xu, S.; Qian, Y. Accounts of Chemical Research 2000, 33, 457.
17. Miyake, T.; Tanii, T.; Kato, K.; Hosaka, T.; Kanari, Y.; Sonobe, H.; Ohdomari, I. Chemical Physics Letters 2006 426 361.
18. Ryan, D.; Parviz, B. A.; Linder, V.; Semetey, V.; Sia, S. K.; Su, J.; Mrksich, M.; Whitesides, G. M. Langmuir 2004, 20, 9080.
19. Harnett, C. K.; Satyalakshmi, K. M.; Craighead, H. G. Applied Physics Letters 2000, 76, 2466.
20. Eck W.; Stadler V.; Geyer W.; Zharnikov, M.; G€olzh€auser, A.; Grunze, M. Adv. Mater. 2000, 12, 805.
21. Harnett, C. K.; Satyalakshmi, K. M.; Craighead, H. G. Langmuir 2001, 17, 178.
22. N. Hadjichristidis, S. Pispas, G. Floudas, Block Copolymers: Synthetic Strategies, Physical Properties, and Applications, John Wiley and Sons, Hoboken, N.J., 2003.
23. G. M. McClelland, M. W. Hart, C. T. Rettner, M. E. Best, K. R. Carter, and B. D. Terris, "Nanoscale patterning of magnetic islands by imprint lithography using a flexible mold," Applied Physics Letters, 81, 1483 (2002).
24. D. H. Kim, Z. Lin, H.-C. Kim, U. Jeong, and T. P. Russell, "On the replication of block copolymer templates by poly (dimethylsiloxane) elastomers," Advanced Materials, 15, 811 (2003).
25. Y. S. Kim, H. H. Lee, and P. T. Hammond, "High density nanostructure transfer in soft molding using polyurethane acrylate molds and polyelectrolyte multilayers," Nanotechnology, 14, 1140 (2003).
26. L. Rockford, S. G. J. Mochrie, and T. P. Russell, "Propagation of Nanopatterned Sustrate Templated Ordering of Block Copolymers in Thick Films," Macromolecules, 34, 1487 (2001).
27. X. M. Yang, R. D. Peters, T. K. Kim, P. F. Nealy, S. L. Brandow, M-S. Chen, L. M. Shirey, and W. J. Dressick, "Proximity X-ray Lithography Using Self-Assembled Alkylsilixone Films Resolution and Pattern Transfer," Langmuir, 17, 228 (2001).
28. E. Schaffer, T. Thurn-Albrecht, T. P. Russell, and U. Steiner, "Electrically Induced Structure Formation and Pattern Transfer," Nature, 403(6772) 874 (2000).
29. T. Thurn-Albrecht, J. DeRouchy, T. P. Russell, and H. M. Jaeger, "Overcoming Interfacial Interactions with Electric Fields," Macromolecules, 33, 3250 (2000).
30. S. O. Kim, H. H. Solak, M. P. Stoykovich, N. J. Ferrier, J. J. DePablo, and P. F. Nealy, "Epitaxial Self-Assembly of Block Copolymers on Lithographically Defined Nanopatterned Substrates," Nature, 424, 411, (2003).
31. Kasama, K. Optronics 2003, 256, 106.
32. López, G.; Biebuyck, H. A.; Whitesides, G. M. Langmuir 1993, 9, 1513.
33. Anderson, M. A.; Srinivasan, C.; Hohman, J. N.; Carter, E. M.; Horn, M. W.; Weiss, P. S. Adv. Mater. 2006, 18, 3258.
34. Mooney, J. F., Hunt, A. J., McIntosh, J. R., Liberko, C. A., Walba, D. M., Rogers, C. T., Proc. Natl. Acad. Sci. USA 1996, 93, 12287.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A method of fabricating a patterned nanosubstrate, the method comprising:
   (a) providing a substrate coated with a resist layer;
   (b) forming a nanoscale pattern in the resist layer by lithography, wherein the pattern comprises one or more first regions essentially devoid of resist and one or more second regions comprising resist;
   (c) plasma treating the one or more first regions;
   (d) forming a monolayer of first amphiphiles in the one or more first regions by self assembly;
   (e) removing resist from the one or more second regions; and
   (f) coupling a functional agent to distal ends of at least a portion of the first amphiphiles, wherein the functional agent is a biomolecule, cell, or functionalized nanoelement, and wherein said coupling is performed in less than 1 minute.

2. The method of claim 1, further comprising:
   (g) forming a monolayer of second amphiphiles in the one or more second regions.

3. The method of claim 2, further comprising:
   (h) coupling a second functional agent to the distal ends of at least a portion of the second amphiphiles.

4. The method of claim 1, wherein the functional agent is selected from the group consisting of antibodies, enzymes, proteins, ligands for cell surface receptors, nucleic acids, cells, and a combination thereof.

5. The method of claim 1, wherein the substrate comprises a metal layer beneath the resist layer, and wherein the metal layer comprises a metal selected from the group consisting of Au, Ag, Cu, Cr, and a combination thereof.

6. The method of claim 1, wherein the substrate comprises a base layer beneath the metal layer.

7. The method of claim 6, wherein the base layer comprises silicon or silicon dioxide.

8. The method of claim 2, wherein the first and second amphiphiles are alkanethiols.

9. The method of claim 1, wherein at least a portion of the first amphiphile comprises a terminal functional group selected from the group consisting of an amino group, a carboxyl group, a sulfhydryl group, and a hydroxyl group.

10. The method of claim 1, wherein the resist is PMMA.

11. The method of claim 1, wherein the one or more first regions or the one or more second regions comprise at least one feature having a dimension smaller than 15 nm.

12. The method of claim 2, wherein the base layer is silicon, the metal layer is gold, the first amphiphile is 11-amino-1-undecanethiol, and the second amphiphile is 1-octadecanethiol.

13. The method of claim 5, wherein the metal layer is from 50 to 150 nm in thickness.

14. The method of claim 1, wherein the resist layer is from 50 to 200 nm in thickness.

15. The method of claim 1, wherein a predetermined nanoscale pattern of alternating hydrophilic and hydrophobic regions is established on the surface of the nanosubstrate.

16. The method of claim 1, wherein a predetermined nanoscale pattern of functional groups is established on the surface of the nanosubstrate.

17. The method of claim 16, wherein the functional groups are amino groups.

18. The method of claim 1, wherein the lithography is selected from the group consisting of electron beam lithography, photolithography, ion beam lithography, and nanoimprint lithography.

19. The method of claim 3, wherein the second functional agent is selected from the group consisting of antibodies, enzymes, proteins, ligands for cell surface receptors, nucleic acids, cells, and a combination thereof.

20. The method of claim 3, wherein a predetermined nanoscale pattern of functional groups is established on the surface of the nanosubstrate.

21. The method of claim 1, wherein the step of plasma treating comprises treating with a plasma comprising oxygen.

22. The method of claim 1, wherein the step of removing resist comprises extensive solvent extraction to remove all traces of the resist.

23. The method of claim 3, wherein one of said functional agent and said second functional agent is hydrophilic and the other is hydrophobic.

24. The method of claim 23, wherein the functional agent and second functional agent are coupled to the first and second amphiphiles by a process comprising spin coating a mixture of the functional agent and the second functional agent onto the surfaces of the first and second amphiphile monolayers.

25. The method of claim 2, wherein the first and second amphiphiles form monolayers of different thicknesses.

* * * * *